(12) United States Patent
Murphy et al.

(10) Patent No.: US 6,309,817 B1
(45) Date of Patent: Oct. 30, 2001

(54) IDENTIFICATION OF VIRULENCE DETERMINANTS ACTIVATORS IN PROKARYOTIC PATHOGENS

(75) Inventors: John R. Murphy, Boston, MA (US); Li Sun, Oxford (GB)

(73) Assignee: Boston Medical Center Corporation, Boston, MA (US)

( * ) Notice: Subject to any disclaimer, the term of this patent is extended or adjusted under 35 U.S.C. 154(b) by 0 days.

(21) Appl. No.: 09/408,618

(22) Filed: Sep. 30, 1999

Related U.S. Application Data
(60) Provisional application No. 60/102,545, filed on Sep. 30, 1998.

(51) Int. Cl.[7] .................................................. C12Q 1/00
(52) U.S. Cl. .................. 435/4; 435/6; 435/7.32; 435/69.1; 435/320.1; 536/23.1; 536/23.4; 935/23; 935/33; 935/38; 935/41; 935/47; 935/72; 935/73
(58) Field of Search ...................... 435/4, 6, 7, 32, 435/69.1, 320.1; 514/44; 536/23.1, 23.4; 935/23, 33, 38, 47, 73, 41, 72

(56) References Cited

U.S. PATENT DOCUMENTS

| | | | |
|---|---|---|---|
| 5,338,664 | 8/1994 | Tuckman et al. | 435/4 |
| 5,780,278 | 7/1998 | Miller et al. | 435/172.2 |
| 5,876,931 | 3/1999 | Holden | 435/6 |
| 5,948,641 | 9/1999 | Lal et al. | 435/69.1 |
| 5,965,368 | 10/1999 | Vidal et al. | 435/6 |
| 5,976,832 | 11/1999 | Hitomi et al. | 435/69.1 |
| 6,004,354 | 12/1999 | Miller et al. | 935/78 |
| 6,004,764 | 12/1999 | Bishai et al. | 435/7.8 |
| 6,010,901 | 1/2000 | Miller, III et al. | 435/320.1 |
| 6,015,669 | 1/2000 | Holden | 435/6 |
| 6,022,863 | 2/2000 | Peyman | 514/44 |

OTHER PUBLICATIONS

Escolar et al. Coordinated repression in vitro of divergent fepA–fes promoters of *E. coli* by the iron uptake regulation (Fur) protein. Journal of BActeriology (1998) vol. 180, No. 9. pp. 2579–2582.*
Promega Notes Magazine No. 58, 1996.*
Tao, et al., Proc. Natl. Acad. Sci. USA 89:5897–5901 (1992).
Schmitt, et al., Infect. Immun. 59:1899–1904 (1991).
Boyd, et al., Proc. Natl. Acad. Sci. USA 87:5968–5972 (1990).
Ding, et al., Nature Struct. Biol. 3(4):382–387 (1996).
Schiering, et al., Proc. Natl. Acad. Sci. USA 92:9843–9850 (1995).
White, et al., Nature 394:502–506 (1998).
Tao, et al., Proc. Natl. Acad. Sci. USA 90:8524–8528 (1993).
Tao, et al., Mol. Microb. 14(2): 191–197 (1994).
Boyd, et al., J. Bacteriol. 174:1268–1272 (1992).
Schmitt, et al., Infect. Immun. 59:3903–3908 (1991).
Schmitt, et al., Infect Immun. 63(11):4284–4289 (1995).
Doukhan, et al., Gene 165(1):67–70 (1995).
Oguiza, et al., J. Bacteriol. 177(2):465–467 (1995).
Günter, et al., J. Bacteriol. 175:3295–3302 (1993).
Unger, et al., Gene 31(3): 103–108 (1984).
Schmitt, et al., J. Bacteriol. 176:1141–1149 (1994).
Schmitt, J. Bacteriol. 178:838–845 (1997).
Gish, et al., Nature Genet. 3:266–272 (1993).
Madden et al., Meth. Enzymol. 266:131–141 (1996).
Altschul, et al., Nucleic Acids Res. 25:3389–3402 (1997).
Zhang, et al., Genome Res. 7:649–656 (1997).
Kaczorek. et al., Science 221:855–858 (1983).
Greenfield, et al., Proc. Natl. Acad. Sci. USA 80:6853–6857 (1983).
Ratti, et al., Nucleic Acids Res. 11:6589–6595 (1983).
Fourel, et al., Infect. Immunol. 57:3221–3225 (1989).
Boyd, et al., J. Bacteriol. 170:5949–5952 (1988).
Tao, et al. , Proc. Natl. Acad. Sci. USA 91:9646–9650 (1994).
Althaus, et al., Biochem. 38:6559–6569 (1999).
Hantke, Mol. Gen. Genet. 197:337–341 (1984).
Schaffer, et al., Mol. Gen. Genet. 200:111–113 (1985).
Litwin, et al., J. Bacteriol. 174:1897–1903 (1992).
Prince, et al., J. Bacteriol. 175:2589–2598 (1993).
Staggs, et al., J. Bacteriol. 173:417–425 (1991).
Stojiljkovic, et al., J. Mol. Biol. 236:531–545 (1994).
Schmitt, et al., Infection and Immunity, 65(12):5364–5367 (1997).
Dussurget, et al., Trends in Microbiology, 6(9):354–358 (1998).
Sun, et al., "DtxR: Structure, Function and Molecular Genetics of an Iron–Activated Repressor," in Hacker, et al. (eds.), *Bacterial Protein Toxins*, Zent.bl.Bakteriol. Suppl. 29, Gustav Fischer (1998).
Barrett, et al., Proc. Natl. Acad. Sci. USA 95:5317–5322 (1998).
Shroff, et al., Infection and Immunity 63:3904–3913 (1995).
The World Health Report 1996, Fighting disease Fostering development, Executive Summary, World Health Organization, Geneva.

* cited by examiner

*Primary Examiner*—Jeffrey Stucker
*Assistant Examiner*—Ulrike Winkler
(74) *Attorney, Agent, or Firm*—Lerner, David, Littenberg, Krumholz & Mentlik, LLP

(57) ABSTRACT

Disclosed is a method for identifying activators of a transition metal-dependent repressor of virulence gene expression in infectious prokaryotic pathogens. The method utilizes genetic circuitry that represents the response of a given prokaryote to nutritional stress and the expression of genes that contribute to the establishment of the infectious process. The exposure of recombinant cells or a cell-free system containing the genetic circuitry to a non-metal ion test substance that activates the repressor produces a detectable response. The method is applicable for any prokaryote employing metal ion-dependent repressors to regulate specific gene expression, specifically as it pertains to virulence determinant expression.

17 Claims, 3 Drawing Sheets

IDENTIFICATION OF VIRULENCE DETERMINANTS ACTIVATORS IN PROKARYOTIC PATHOGENS

This application claims priority under 35 U.S.C. § 119(e) from Provisional Application No. 60/102,545, filed Sep. 30, 1998, the contents of which are hereby incorporated by reference in their entirety.

GOVERNMENT SUPPORT

Applicants' invention was supported in part by Public Health Service Grant AI-21628 from the National Institute of Allergy and Infectious Diseases. Therefore, the government may have certain rights in the invention.

FIELD OF THE INVENTION

The present invention relates to methods of identifying substances that combat infections and diseases caused by prokaryotes, and more particularly to methods of identifying substances that exhibit anti-bacterial/anti-microbial effects.

BACKGROUND OF THE INVENTION

As a consequence of the widespread use and perhaps even misuse of antibacterial drugs, strains of drug-resistant pathogens have emerged. Antibiotic-resistant bacterial strains have been associated with a variety of infections, including tuberculosis, gonorrhea, staphylococcal and pneumococcal infections, and the bacteria most commonly associated with pneumonia, ear infections and meningitis. More importantly, infectious disease remains the largest cause of mortality in the world.

The typical response to an ineffective antibiotic has simply been change antibiotics. Unfortunately, this alternative no longer offers a guarantee of success. For example, certain strains of enterococci are resistant to vancomycin—a drug formerly considered to be the ultimate weapon against many different types of bacteria. The World Health Organization has expressed concern that the development of new drugs is not keeping pace with the numbers of antibiotics which become ineffective. World Health Report 1996: Fighting Disease, Fostering Development, Executive Summary (World Health Organization 1996). Despite ongoing research, there remains a pressing need to develop new antibiotics. There is also a need for antibacterials that are effective in treating disease while not stimulating the emergence of resistant strains.

Bacteria respond to nutritional stress by the coordinated expression of different genes. This facilitates their survival in different environments. Among these differentially regulated genes are the genes responsible for the expression of virulence determinants. The expression of these genes in a sensitive or susceptible host allows for the establishment and maintenance of infection or disease. Virulence genes encode toxins, colonization factors and genes required for siderophores production or other factors that promote this process.

Virulence genes in bacteria express a variety of factors that allow the organism to invade, colonize and initiate an infection in humans and/or animals. These genes are not necessarily expressed constantly (constitutively), however. That is, the bacterium is not always "infectious". In many circumstances, the expression of virulence genes is controlled by regulatory proteins known as repressors in conjunction with a corresponding operon(s) or operator(s). In prokaryotes, one class of repressors is activated upon binding to or forming a complex with a transition metal ion such as iron or zinc. When the repressor is activated, it binds the operator thereby preventing production of virulence determinants.

Virulence determinants are most often expressed when the bacterial pathogen is exposed to nutritional stress. An iron-poor environment is an example of such a condition. In this environment, insufficient iron is present to maintain the repressor in its active state. In the inactive form, the repressor cannot bind to target operators. As a result, virulence genes are de-repressed and the bacterium is able to initiate, establish, promote or maintain infection.

The expression of these virulence determinants is in many bacterial species is co-regulated by metal ions. In many instances the metal co-factor that is involved in vivo is iron. In the presence of iron, the repressor is activated and virulence gene expression is halted.

This pattern of gene regulation is illustrated by the following example. The bacterium that causes diphtheria produces one of the most potent toxins known to man. The toxin is only produced under conditions of iron deprivation. In the presence of iron, the bacterial repressor (which in this species is known as diphtheria toxin repressor protein, abbreviated "DtxR") binds iron and undergoes conformational changes that activate it and allow it to bind a specific DNA sequence called the tox operator. The tox operator is a specific consensus DNA sequence found upstream of the gene that produces the diphtheria toxin. Binding of DtxR to this site thereby prevents toxin expression. Typically, during infection of a human or animal host the diphtheria bacillus (or other pathogenic/opportunistic bacteria) grows in an environment that rapidly becomes restricted in several key nutrients. Paramount among these essential nutrients is iron, and when iron becomes limiting the diphtheria bacillus begins to produce the toxin. Moreover, the constellation of virulence genes that DtxR controls becomes de-repressed and the diphtheria bacillus becomes better adapted to cause an infection. In the case of diphtheria, the toxin kills host cells thereby releasing required nutrients including iron.

SUMMARY OF THE INVENTION

The present invention is directed to a simple and accurate method for identifying substances that repress or prevent or attenuate virulence gene expression in an infectious microorganism and phenotypically convert it to a non-pathogen. The method may be practiced to identify substances effective against any pathogenic (infectious) prokaryote whose pattern of virulence determinant expression (or a portion thereof) is under the regulatory control of a metal ion-dependent repressor. Thus, Applicants' invention can be employed to identify substances that provide a therapeutic or medicinal benefit to humans and animals.

A first aspect of the present invention is directed to a method for screening test substances to identify non-metal ion activators of a metal ion-dependent repressor of virulence determinants expression in a virulent or opportunistic prokaryotic pathogen. Substances that are identified as activators of the repressor may be developed as antibiotics or anti-bacterial substances. Accordingly, this method involves:

(a) providing recombinant cells comprising a first recombinant DNA segment containing a first promoter operably linked to a first regulatory gene encoding a first repressor native to or functional in a given prokaryote, a second DNA segment containing a second promoter operably linked to a first operator that binds said first repressor and a second regulatory gene encoding a second repressor, and a third recombinant DNA segment comprising a third promoter operably linked to a second operator that binds the second repressor, and a reporter gene;

(b) culturing said recombinant cells in medium substantially free of metal ion activators of said first repressor and which contains a selection agent that directly or indirectly causes a detectable response upon expression or lack of expression of the reporter gene;

(c) adding a non-metal ion test substance to said medium; and (d) determining whether the response occurs as an indication of whether said test substance activates said first repressor.

In preferred embodiments, the first regulatory gene encodes a diphtheria tox repressor (DtxR) protein that is the native DtxR protein, or a fragment, variant or homologue of DtxR, and the first operator binds the DtxR protein and is native tox operator (toxo) or a toxo fragment, or a variant of a DtxR consensus binding sequence. In more preferred embodiments the second regulatory gene encodes the tetracycline repressor (TetR), the second operator comprises the tetracycline operator (tetO), the reporter gene encodes chloramphenicol acetyltransferase and the selection agent is chloramphenicol. The medium comprises a chelating agent that binds metal ion activators of the first repressor.

In other preferred embodiments, the first and second recombinant DNA segments are contained in a first vector, preferably a plasmid, and the third recombinant DNA segment is contained in a second vector such a lysogenic phage.

Another embodiment of this aspect of the invention entails providing a solution containing (a) purified repressor native to or functional in a given prokaryote; (b) a DNA construct comprising in operable association, a promoter, an operator and a reporter gene; (c) a coupled transcriptional and translational system that allows expression of the reporter gene; (d) a chelating agent that binds metal activators of the repressor; and (e) a non-metal ion test substance to allow a reaction to occur; and detecting expression or lack of expression of the reporter gene as an indication of whether the test substance activates the repressor. This embodiment offers relative simplicity in terms of working in a cell-free system with fewer elements and genetic manipulations. In preferred embodiments, the coupled transcriptional and translational system contains bacterial extract and the reporter gene encodes β-galactosidase or luciferase or a readily assayable reaction product.

Another aspect of the present invention is directed to the various genetic constructs and compositions of matter useful in the disclosed methods. Accordingly, one preferred embodiment is directed to a composition of matter containing: a recombinant vector comprising a first DNA segment containing a first promoter operably linked to a first regulatory gene encoding a first repressor native to or functional in a given prokaryote, and a second DNA segment containing a second promoter operably linked to a first operator that binds the first repressor, and a second regulatory gene encoding a second repressor. The recombinant vector further may contain a third DNA segment containing a third promoter operably linked to a second operator that binds the second repressor, and a reporter gene. It is preferred, however, that the third DNA segment resides on a separate vector such as a lysogenic phage. This aspect of the present invention also provides recombinant host cells, e.g., E. coli containing the recombinant vector(s).

Another embodiment of this aspect of the present invention provides a composition of matter containing: (a) purified repressor protein native to or functional in a given prokaryote, a, (b) a DNA construct comprising in operable association, a promoter, an operator that binds the repressor protein and a reporter gene, (c) a transcriptional and translational system that allows expression of the reporter gene and (d) a chelating agent that binds metal ion activators of said repressor protein. The composition further may contain a non-metal ion test substance. In preferred embodiments, the coupled system comprises bacterial extract.

DETAILED DESCRIPTION OF THE INVENTION

Figure 1:
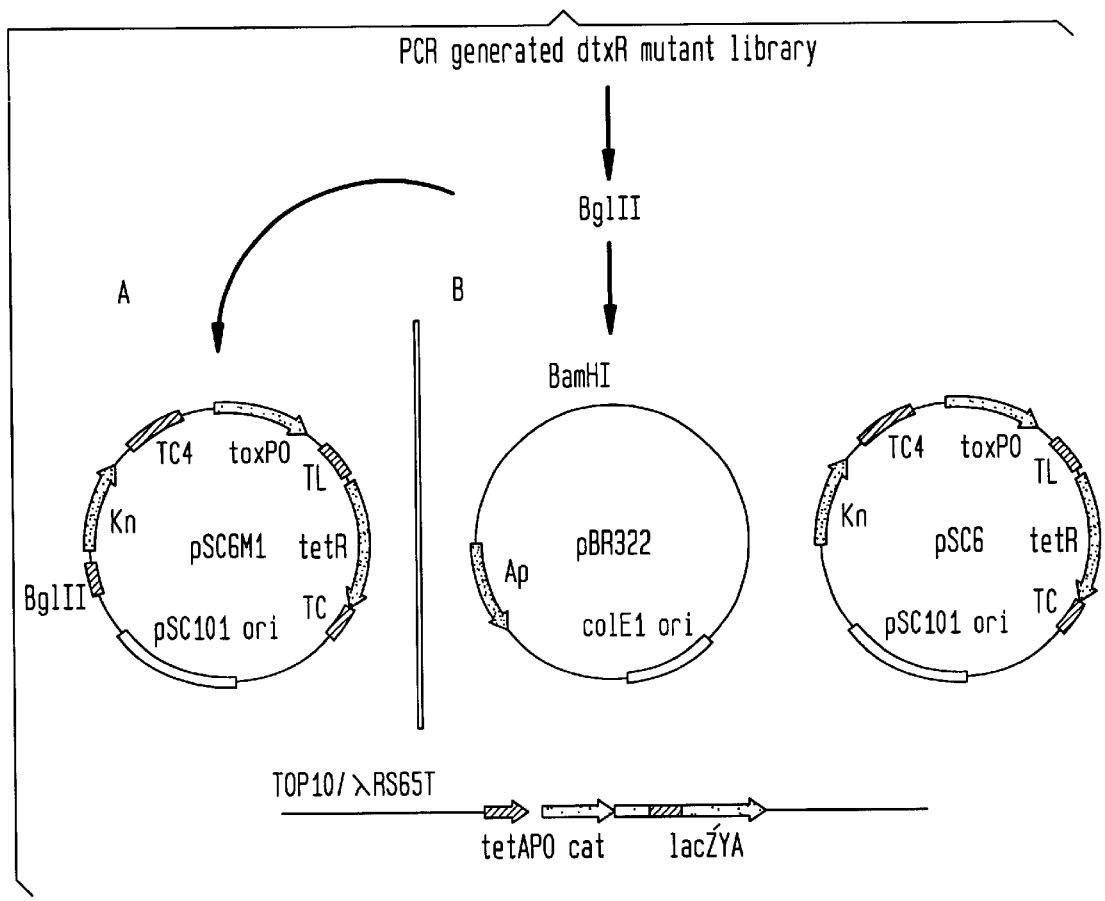
FIG. 1 schematically illustrates the plasmids and constructs employed by the PSDT (positive selection of DtxR homologue and targets) system to identify iron-independent repressors. Randomly PCR generated mutants of the DtxR were cloned into the BamHl site of pBR322 and then co-transformed into the PSDT indicator strain E. coli TOP10λRS65T with pSC6. Alternatively, mutant dtxR genes were cloned into pSC6M1 and transformed into TOP10λRS65T. Iron independent mutants conferred $Cm^R$ were selected on Ap/Kn/Cm/DP (Ap=Ampicillin; Kn=Kanamycin; Cm=Chloramphenicol; DP=2, 2'-dipyridyl).

The presently disclosed method is designed to identify non-metal ion substances that phenotypically convert a virulent or opportunistic pathogenic prokaryote such as a bacterium or microbe into a non-pathogenic microorganism. The method entails the use of genetic circuitry that mimics key, interrelated events that occur in vivo and cause a given prokaryote to become infectious or pathogenic. This system contains a small group of interrelated genetic elements. The introduction into the system of a test substance causes these genetic elements to respond in an easily detectable manner.

The regulatory units e.g., the first, second and third promoters, may be the same or different. They are functional in the cell of choice and they are constitutive or inducible in nature upon the addition of the appropriate inducer to the medium direct the continuous expression of the operably linked gene or genes. Regulatory units are well known in the art. Examples include lacI, lacO, trpR and trpO.

In preferred embodiments, the first repressor encodes DtxR or a functional fragment, variant or homologue (collectively referred to as "a DtxR protein"). DtxR is an iron-dependent DNA-binding protein having a deduced molecular weight of 25,316 and which functions as a global regulatory element for a variety of genes on the *C. diphtheriae* chromosome. See Tao et al., Proc. Natl. Acad. Sci. USA 89:5897–5901 (1992); Schmitt et al., Infect. Immun. 59:1899–1904 (1994). For example, DtxR regulates the expression of the diphtheria toxin structural gene (tox) in a family of closely related Corynebacteriophages. The DtxR gene has been cloned and sequenced in *E. coli* and its DNA and amino acid sequences have been reported. See Boyd et al., Proc. Natl. Acad. Sci. USA 87:5968–5972 (1990); Schmitt et al., supra. DtxR is activated by divalent transition metal ions (e.g., iron). Once activated, it specifically binds the diphtheria tox operator and other related palindromic DNA targets. See Ding et al., Nature Struct. Biol. 3(4) :382–387 (1996); Schiering et al. Proc. Natl. Acad. Sci. USA 92:9843–9850 (1995); White et al., Nature 394:502–506 (1998).

Functional fragments or variants of DtxR, when activated, retain their binding activity to the tox operator (or a functional fragment thereof) and/or the DtxR consensus binding sequence. DtxR fragments and variants can be identified by standard techniques such as mutagenesis. It has been reported that the Cys102 residue in DtxR is important in binding the tox operator and substitutions with amino acids other than Asp abolish binding activity. Tao et al., Proc. Natl. Acad. Sci. USA 90:8524–8528 (1993). Other variants are disclosed in Tao et al., Mol. Microb. 14(2):191–197 (1994). Tao discloses that some DtxR alleles have different amino acid sequences, e.g., the DtxR allele from strain 1030(−) of *C. diphtheriae* was found to carry six amino acid substitutions in the C-terminal region, none of which affected the iron-dependent regulatory activity of DtxR (1030) (Tao 1994). See also Boyd et al., J. Bacteriol. 174:1268–1272 (1992) and Schmitt et al., Infect. Immun. 59:3903–3908 (1991).

Many other bacterial species employ regulatory circuits and repressor proteins that exhibit high degrees of sequence similarity to DtxR. Thus, DtxR homologues may also be employed in the methods of the present invention. Iron dependent regulator (IdeR), isolated from *Mycobacterium tuberculosis*, has been found to share 60% homology or sequence similarity with DtxR. See Schmitt et al., Infect Immun. 63(11):4284–4289 (1995). See also Doukhan et al., Gene 165(1):67–70 (1995), which reports and references DtxR homologues in *Mycobacterium smegmatis* and *Mycobacterium leprae*. DtxR homologues have been cloned from other gram-positive organisms including *Brevibacterium lactofermentum* and *Streptomyces lividans*. See Oguiza et al., J. Bacteriol. 177(2):465-467 (1995); Günter et al., J. Bacteriol. 175:3295–3302 (1993); and Schmitt et al., Infect. Immun. 63:4284–4289 (1995). Staphylococcal iron regulated repressor (SirR), native to *Staphylococcus epidermitis*, is another known DtxR homologue. These proteins bear a common feature—they share a remarkably high sequence similarity in the respective N-terminal 139 amino acids, especially those amino acids involved in DNA recognition and transition metal ion co-ordination. In addition to DtxR homologues, DtxR sensitive promoters and/or genes involved in a variety of cellular activities have been cloned from *C. diphtheriae* chromosomal libraries. See Schmitt et al., J. Bacteriol. 176:1141–1149 (1994), and Schmitt, J. Bacteriol. 179:838–845 (1997).

A collection of accession numbers for sequences that are homologous to DtxR, or contain the consensus toxO sequence, is presented in Table 1. See also, Altschul, et al., J. Mol. Biol. 215:403–410 (1990); Gish, et al., Nature Genet. 3:266–272 (1993); Madden, et al., Meth. Enzymol. 266:131–141 (1996); Altschul, et al., Nucleic Acids Res. 25:3389–3402 (1997); and Zhang, et al., Genome Res. 7:649–656 (1997). This degree of sequence similarity in the homologues and the distribution of the operator sequences indicates that the iron regulatory pathway that employs the DtxR-family of repressors is conserved in many important human and animal pathogens.

TABLE 1

DtxR Homologues

| Pathogenic | Human/Veterinary | Applications | Other | |
|---|---|---|---|---|
| CAA67572 | *S. epidermidis* | * | L35906 | *C. glutamicum* |
| Gi 1777937 | *T. pallidum* | | Z50048 | *S. pilosus* |
| CAA15583 | *M. tuberculosis* | * | Z50049 | *S. lividans* |
| U14191 | *M. tuberculosis* | * | U14190 | *M. smegmatis* |
| L78826 | *M. leprae* | * | L35906 | *B. lactofermentum* |
| M80336 | *C. diphtheriae* | * | | |
| M80337 | *C. diphtheriae* | * | | |
| M34239 | *C. diphtheriae* | * | | |
| M80338 | *C. diphtheriae* | * | | |

Selection of DNA Homologous to DtxR Identifiable in Current Databases

| | | | |
|---|---|---|---|
| Gi 2622034 | *M.thermoautotrophicum* | Stanford 382 | *S. meliloti* |
| Gi 2621260 | *M.thermoautotrophicum* | TIGR 1280 | *S. aureus* |
| M50379 | *M. jannaschi* | OUACGT | *S. pyogenes* |
| Q57988 | *M. jannaschi* | Sanger 518 | *B. bronchoseptica* |
| O33812 | *S. xylosus* | Sanger 1765 | *M. bovis* * |
| Gi 264870 | *A fulgidus* | Sanger 520 | *B. pertusis* * |
| Gi 2648555 | *A fulgidus* | WUGSC | *K. pneumoniea* |
| Gi 2650396 | *A fulgidus* | TIGR 76 | *C. crescentus* |
| Gi2650706 | *A fulgidus* | TIGR 24 | *S. putrificacieus* |
| BAA79503 | *A. pernix* | TIGR1351 | *E. faecalis* |
| AAD18491 | *C. pneumoniae* * | AE000783 | *B. burgdorferi* |
| Gi 3328463 | *C. trachomatis* | TIGR1313 | *S. pneumoniea* * |

TABLE 1-continued

DtxR Homologues

| | | |
|---|---|---|
| CAB49983.1 *P. abyssi* | Snager 632 | *Y. pestis* |
| BAA30263 *P. horikoshi* | AE000657 | *A. aeolius* |
| Gi 2621260 *M.thermoautotrophicum* | TIGR 920 | *T. ferrooxidans* |
| TIGR 1752 *V. cholera* | AE001439 | *H. pylori* |

* = species also contains toxO sequences

In the case where the first repressor is DtXR, the preferred first operator is the natively associated tox operator, toxO, a functional fragment thereof, or a variant of a DtxR consensus binding sequence. The native tox operator (i.e., 5'-ATAATTAGGATAGCTTTACCTAATTAT-3' (SEQ ID NO:1)) is a 27 base pair interrupted palindromic sequence upstream of the diphtheria tox structural gene; it features a 9-base pair inverted repeat sequence that is separated by 9 base pairs. See Kaczorek et al., Science 221:855–858 (1983); Greenfield et al., Proc. Natl. Acad. Sci. USA 80:6853–6857 (1983); Ratti et al., Nucleic Acids Res. 11:6589–6595 (1983); and Fourel et al., Infect. Immunol. 57:3221–3225 (1989). It overlaps both the −10 region of the tox promoter and the transcriptional start sites at −45, −40 and −39 upstream of the diphtheria toxin structural gene. See Boyd et al., J. Bacteriol. 170:5940–5952 (1988). The minimal essential DNA target site, i.e., 5'-GTAGGTTAGGCTAACCTAT-3' (SEQ ID NO:2), is a 19 base pair sequence that forms a perfect palindrome around a central C or G. It is described in Tao and Murphy, Proc. Natl. Acad. Sci. USA 91:9646–9650 (1994). In preferred embodiments, the native promoter $P_{tOX}$ is operably linked to the operator, resulting in the construct known as toxPO. Also preferred are variants of toxo based on the DtxR consensus-binding sequence (5'-ANANTTAGGNTAGNCTANNCTNNNN-3' (SEQ ID NO:3)). The variants are defined by the following sequence: 5'-TWAGGTTAGSCTAACCTWA-3' (SEQ ID NO:4).

In yet other preferred embodiments, the first repressor is fur (ferric uptake regulator), or a functional fragment or variant thereof. Fur functions as a metal ion-activated global regulatory element for a variety of genes in gram-negative bacteria, such as *E. coli*, Pseudomonas, *Vibrio cholerae, Yersinia pestis*, Pseudomonas and Salmonella. See, Althaus, et al., Biochem. 38:6559–6569 (1999), which reports that Fur is activated by zinc ions. Fur and fur-like proteins are also described in Hantke, Mol. Gen. Genet. 197:337–341 (1984); Schaffer et al., Mol. Gen. Genet. 200:111–113 (1985); Litwin et al., J. Bacteriol. 174:1897–1903 (1992); Prince et al., J. Bacteriol. 175:2589–2598 (199); and Staggs et al., J. Bacteriol. 173:417–425 (1991). As in the case of DtxR, the amino acid sequence of the Fur family of regulatory proteins and the nucleic acid sequences of their respective DNA binding sites have been found to be homologous. In embodiments wherein the first repressor is a Fur protein, the corresponding first operator is can be one of several fur box or iron box sequences for example; 5'-GATAATTGAGAATCATTTTC-3', (SEQ ID NO:5) 5'-GATATTGAGAATCATTTTC-3' (SEQ ID NO:6), 5'-GATACTGAGAATCATTTTC-3' (SEQ ID NO:7), 5'-GATACTGAGAATCATGTTC-3' (SEQ ID NO:8) as described in Stojiljkovic et al., J. Mol. Biol. 236:531–545 (1994)).

When the first repressor is a DtxR homologue, the corresponding first operator sequence may be obtained in accordance with routine screening as illustrated in example 2, below. In other embodiments, the first repressor/first operator pair are native to the target prokaryote. In general, however, the target prokaryote need not necessarily dictate the choice of these elements. To identify and develop an antimicrobial to treat Staphylococcus infections, for example, relatively large numbers of test substances may be screened first by using the more preferred pair, DtxR/toxO. The underlying assumption is that the interaction/affinity of repressors in other species for their cognate operators is similar or identical to DtxR/toxO. The next phase of development entails treating Staphylococcus infections with the test substances identified in the first as activators of DtxR. To the extent that any of the test substances are relatively ineffective, a second screen can be conducted, this time replacing DtxR with SirR and toxo with an operator identified from the method described in example 2 (using genomic DNA from Staphylococcal species). Thus, the first repressor is native to or functional in a given prokaryote in the sense that non-native proteins such as fragments and other variants retain binding activity for the corresponding operator, and thus would prevent virulence gene expression in vivo. That is to say, the first repressor co-regulates virulence gene expression in a given prokaryote.

The second DNA segment contains a second promoter, which may be the same as or different from the first promoter, the first operator and a second regulatory gene encoding a second repressor which is different from the first repressor. The second promoter is operably linked to the operator and the second regulatory gene so as to permit the continuous expression of the second regulatory gene unless the first repressor is activated and binds the first operator. The second repressor can be any repressor that will bind a corresponding operator sequence and prevent expression of a gene operably associated with the operator which in this case is the reporter gene. In a preferred embodiment, the second repressor is the tetracycline repressor (TetR) and the second operator on the third DNA fragment is the tetracycline operator (tetO). The nucleotide sequences of tetR and tetO are disclosed in Unger et al., Gene 31(3):103–108 (1984). The second repressor binds the operator of the third DNA segment and prevents expression of the reporter gene. Other second repressor/second operator pairs useful in the present invention include the lac repressor (lacI)/lac operator. The operator must be recognized by the respective repressor.

The third promoter of the third DNA segment is operably linked to the second operator and the reporter gene so as to permit the expression of the reporter gene unless the second repressor binds the second operator.

The choice of promoter for this segment is largely a matter of choice based on the host cell. In the case where the second operator is tetO, however, it is preferred that the promoter is the natively associated tetO promoter such that the resultant construct is tetAPO. In general, the reporter gene may be any gene whose expression product interacts with a corresponding selection agent so as to produce a detectable response. The response may be detected by optical, chemical or photochemical means. In a preferred embodiment, the reporter gene encodes chloramphenicol acetyltransferase. Cells that express this gene grow in the presence of chloramphenicol. If the chloramphenicol acetyltransferase gene is not expressed (e.g., because the candidate substance is not an activator of the first repressor), cell death occurs. Other examples of reporter gene/selection agent combinations are β-lactamase/ampicillin, kanamycin/aminoglycoside phosphotransferase and gentamycin/aminoglycoside acetyltransferase. Some reporter genes allow for selective growth complementation of an auxotroph. An example of such a reporter gene is the gene encoding amylase. In a system using the amylase gene as the reporter gene, cells grown in a medium using starch as the only carbon source (and as the selection agent) will require the expression of amylase to convert starch to carbon. Cells that do not express amylase (indicating that the test substance does not activate the first repressor) fail to grow in the presence of starch.

The DNA segments useful in this invention may be obtained in accordance with standard techniques. For example, they may be generated using standard chemical synthesis techniques. See, e.g., Merrifield, Science 233:341–347 (1986) and Atherton et al., *Solid Phase Synthesis, A Practical Approach*, IRL Press, Oxford (1989). Preferably, they are obtained by recombinant techniques. Standard recombinant procedures are described in Sambrook et al., 1989, *Molecular Cloning, A Laboratory Manual*, Second ed., Cold Spring Harbor, New York, and Ausubel et al., (eds.) *Current Protocols in Molecular Biology*, Green/Wiley, New York (1987 and periodic supplements). The appropriate sequences can be obtained from either genomic or cDNA libraries using standard techniques. DNA constructs encoding the DNA gene segments may also be prepared synthetically by established methods, e.g., in an automatic DNA synthesizer, and then purified, annealed, ligated and cloned into suitable vectors. Atherton et al., supra. Polymerase chain reaction (PCR) techniques can also be used. See e.g., *PCR Protocols: A Guide to Methods and Applications*, 1990, Innis et al. (ed.), Academic Press, New York.

The starting materials in which to make the vectors for use in this aspect of the invention are readily available from commercial sources, e.g., pBR322 and pACYC184 (both available from New England Biolabs). In preferred embodiments, two vectors are utilized. The first vector contains the first and second DNA segments. The choice first vector is based mainly on the host cells. The second vector is preferably a single copy vector, e.g., a lysogenic phage such as a derivative of coliphage lambda (λ) (Simons et al., Gene 53:85–96 (1987)) such that only a single copy of this vector is introduced into the host cell. The presence of only a single copy of the second vector in the recombinant cell ensures that expression of the second repressor prevents expression of the reporter gene, which in turn reduces background noise and false positive results. In less preferred embodiments, the three DNA segments are contained in a single construct or vector. Alternatively, a one-vector system may be utilized, consisting of only three DNA segments. In these embodiments, two selectable marker genes are required. A first marker gene is present to assure maintenance of the vector within the host, and the second marker gene is present to allow detection of the activated first repressor.

Host cells useful in the invention include mammalian, yeast and bacterial cell lines. Bacterial cell lines are preferred. More preferred are *E. coli* cell lines, including DH5α, TOP10 and JM101.

The vectors are introduced into the cells in accordance with standard techniques such as transformation, co-transformation, transfection with a retroviral vector, direct transfection (e.g., mediated by calcium phosphate or DEAE-dextran) and electroporation.

The recombinant cells are cultured via standard techniques. Conditions may vary depending upon the system being used. In general, culturing is continued from about 24 to 48 hours at a temperature between about 30° C. and about 390C., preferably 37° C. The recombinant cells are cultured in a medium substantially free of metal ion that activate the first repressor. Iron is an essential element for both the bacterial pathogen and its animal host; thus, successful competition for this element is an essential component of the infectious process. The concentration of free iron in the mammalian host available to an invading bacterial pathogen is also extremely limited. As a result, the expression of virulence determinants (e.g., colonization factors, siderophores, hemolysins and toxins) by bacterial pathogens is regulated by iron. Accordingly, the cells are cultured in medium substantially free of iron and other metal ions, particularly divalent metal cations, because these elements are activators of DtxR and otherwise would compete with the test substance for binding and cause a false positive selection. A preferred way in which to remove contaminating amounts of the metal ions is to add a chelating agent such as 2,2'-dipyridyl, Chelex™100 (Biorad, Richmond, VA) or transferrin, to the medium. The preferred chelator, 2,2'-dipyridyl, is used at a final concentration of 150–200 μM.

A selection marker is added to the medium. When the chloramphenicol acetyltransferase gene is used as the reporter gene, the selection marker is chloramphenicol. Concentration of chloramphenicol ranges from about 10–15 μg/ml.

The test substance is added to the culture medium, typically at a concentration of no more than about $10^5$ M. A wide variety of test substances may be screened by the present method. Test substances are not limited to any particular type of compound because there may not a preconceived notion as to the nature of the substance that will be recognized and bound by the bacterial repressor protein, and thus serves to activate the protein through tight binding or other chemical interaction. Thus, candidate substances used in the method may be organic or inorganic, polymeric or non-polymeric in nature.

Screening of test substances involves the detection of the expression of the reporter gene of the third DNA gene segment. In a preferred embodiment, the determination as to whether the test substance activates the repressor is made simply by observing whether cell growth occurs. Cell growth may be observed simply by visual inspection. In a preferred embodiment, cell growth is determined by measuring the optical density of a given culture.

Without intending to be bound by any particular theory of operation, the genetic circuitry entailed by the method as broadly described works as follows. If the test substance activates the first repressor, the repressor binds the first operator and prevents expression of the operably linked second regulatory gene (encoding the second repressor). The absence of the second repressor allows the expression of the reporter gene because the second operator is not bound with the second repressor. The reporter gene expression product inactivates the selection marker and thus allows the transformed cells to grow in the medium.

Conversely, if the test substance does not activate the first repressor, expression of the second regulatory gene occurs;

the second repressor binds the second operator, and the reporter gene is not expressed. The lack of expression of the reporter gene renders the cells sensitive to the selection agent and results in the death of the transformed cells. Cell growth does not occur.

Stated in the context of the more preferred embodiment, a test substance that activates DtxR causes DtXR to bind the tox operator and prevent expression of the tetR gene. Because the tetR gene is not expressed, the tetracycline operator (tetO) on the second vector is not bound and the chloramphenicol acetyltransferase-encoding gene is expressed. Chloramphenicol is normally toxic to *E. coli*. Chloramphenicol acetyltransferase inactivates chloramphenicol thus allowing cells to grow in the presence of chloramphenicol. Conversely, if the test substance does not activate DtxR, toxO is not bound and tetR is expressed. Expression of tetR causes binding of TetR to teto, thus preventing expression of chloramphenicol acetyltransferase. In the absence of chloramphenicol acetyltransferase, chloramphenicol exerts its toxic effects and cell growth does not occur.

Thus, in a preferred embodiment, this system is simply a growth/no-growth assay, wherein growth indicates that the candidate substances and activator of DtxR, and the absence of growth (cell death) indicates that the candidate substance is not an activator of the virulence determinant repressor.

Another embodiment of the present invention entails a cell-free system. This embodiment is simpler in that is requires fewer elements and manipulations, namely: (a) purified repressor protein native to or functional in a given prokaryote, (b) a DNA construct comprising in operable association, a promoter, an operator that binds the repressor protein and a reporter gene, (c) a coupled transcriptional and translational system that allows expression of the reporter gene and (d) a chelating agent that binds metal ion activators of the repressor protein. The system is preferably a bacterial extract which is commercially available. The test substance is added and the expression of the reporter gene is detected as an indication of whether the test substance activates the repressor. If the test substance is an activator, the reporter gene is not expressed. Preferred reporter genes allow for direct detection of the expression product and include β-galactosidase (see, Miller, J. H. (1972) Experiments in Molecular Genetics (Cold Spring Harbor Lab. Press, Plainview, NY)) and luciferase or a readily assayable reporter gene product.

Test substances that test positively in the disclosed methods may then be subjected to additional tests to confirm whether they activate the first repressor. For example, a candidate substance that tests positively in the screening assay may be subjected to a gel electrophoresis mobility-shift assay. In this assay, the interaction among the candidate substance, a specific protein (the first repressor protein, e.g., DtxR) and a DNA molecule (e.g. the tox operator) is observed. If a test substance activates the first repressor, it will bind the first repressor. In its active form, the repressor will bind the first operator. If binding occurs, this complex formed will have an altered electrophoretic mobility compared to the toxO probe that is not complexed with an activated DtxR. Mobility shifts may be measured autoradiographically. Other confirmatory tests involve repression of other reporter gene expression.

The invention will be further described by reference to the following detailed examples. These examples are provided for purposes of illustration only, and are not intended to limit the scope of the invention described herein.

EXAMPLES

Example 1 describes the consequences of producing iron-independent DtxR repressors and assaying them in the PSDT system. In one embodiment the PSDT screen can be employed to pan compound libraries for non-metal ion activators. Such compounds would be anticipated to constantly activate DtxR and yield an iron-independent phenotype. The example describes how iron-independence can be detected using the PSDT system coupled with a library of mutant DtxR repressors. In this instance, the alteration in the repressor structure by genetic mutation gives rise to the iron-independent phenotype. The screening of mutants is essentially identical to the screening of compounds using the PSDT screen. Of particular importance are the results presented in FIG. 2 which demonstrate that the Self Activating DtxR (SAD) mutants pulled from a library of randomly generated mutants of dtxR repressor genes are iron independent. Thus the PSDT system is an effective tool for the rapid identification of iron-independent repressors or repressors which are activated in the absence of a metal such as iron.

Example 1

Iron Independent Activation of DtxR.

Materials and Methods

Bacterial Strains, Plasmids, Phages, and Medium.

The bacterial strains, plasmids and phages used in this study are described in Results and Table 2.

TABLE 2

| Part A: Strains and Bacteriophage utilized in Examples 1 and 2 | | |
| --- | --- | --- |
| Strains/Phage | Genotype | Source or Reference |
| Strains: | | |
| *E. coli* TOP 10 | mcrA Δ(mrr-hsdRMS-mcrBC) φ80 Δlac ΔM 15 ΔlacX74 deoR recA 1 λ⁻ endA1 | Invitrogen |
| *E. coli* DH5α | F-(φ8Od lacZ ΔM15) Δ(lacZYA-argF) recA1 endA gyrA thi1 hsdR17 (rk⁻, mk⁻) supE44 relA1 U196 | BRL |
| *E. coli* NK7049 | F⁻ λ⁻ ΔlacX74 rspL galOP308 | Simons et al. (1987) |
| *Corynebacterium diphtheriae* C7 (−) | | Boyd et al. (1990) |
| *C. diphtheriae* 484 | | Nakao et al. |

TABLE 2-continued

Part A: Strains and Bacteriophage utilized in Examples 1 and 2

| Strains/Phage | Genotype | Source or Reference |
|---|---|---|
| C. diphtheriae 880 | | (1996) Nakao et al. |
| Brevibacterium ammoniagenes | | (1996) ATCC |
| Bacteriophages: | | |
| λRS45 | lacZ' bla' | Simons et al (1987) |
| λRS65 | tetAPO-cat-lacZYA $Cm^R$ | Tao et al. (1995) |
| λRS65T toxPO | toxPO$^-$ lacZ $Kn^R$ | Boyd et al. (1990) |
| λRS65T | tetAPO-cat-lacZ'YA $Cm^R$ | Tao et al. (1995) |

TABLE 2

Part B: Plasmids utilized in Examples 1 and 2

| Plasmid | Genotype | Source or Reference |
|---|---|---|
| Plasmids: | | |
| pRS551 | lacZYA $AP^R$ $Kn^R$ | Simons et al. (1987) |
| pCM4 | cat $AP^R$ | Pharmacia |
| pGPI-2 | $Kn^R$ | Tabor and Richardson (1987) |
| pWS129 | pSC101 ori $Kn^R$ | Wang et al. (1991) |
| pRS551toxPO | toxPO $AP^R$ $Kn^R$ | Boyd et al. (1990) |
| pXT102C | dtxR $AP^R$ | Tao et al. (1993) |
| PCR/tetRT | tetR TL $AP^R$ $Kn^R$ | These Studies |
| pLS-1 | dtxR $AP^R$ $Kn^R$ | These Studies |
| pLS-2 | dtxR$^-$ $AP^R$ | These Studies |
| pRS65T | cat trpA TC $AP^R$ $Kn^R$ | These Studies |
| pSA20 | $AP^R$ $Kn^R$ | These Studies |
| pSA18M1 | pSC101 ori tetR mtP $Kn^R$ | These Studies |
| pSC6M1 | pSC101 ori tetR toxPO $Kn^R$ | These Studies |
| pBR322 | ColE1 ori $AP^R$ | New England Biolabs |
| pACYC184 | p15A ori $Cm^R$ | Mew England Biolabs |
| pRDA | CoIE1 ori dtxR $AP^R$ | These Studies |
| PSC6 | pSC101 ori toxpO-tetR $Kn^R$ | These Studies |
| pSDM2 | pSC101 ori SAD2 $Kn^R$ | These Studies |
| pSDM3 | pSC101 ori SAD3 $Kn^R$ | These Studies |
| pSDM11 | pSC101 ori SAD11 $Kn^R$ | These Studies |
| pSDM5 | pSC101 ori SAD5 $Kn^R$ | These Studies |
| pDM2 | ColE1 ori SAD2 $AP^R$ | These Studies |
| pDM3 | ColE1 ori SAD3 $AP^R$ | These Studies |
| pDM11 | ColE1 ori SAD11 $AP^R$ | These Studies |
| pDM5 | ColE1 ori SAD5 $AP^R$ | These Studies |
| pDM2A | p15A ori SAD2 $Cm^R$ | These Studies |
| pDM3A | p15A ori SAD3 $Cm^R$ | These Studies |

Tabor, et al., Proc. Natl. Acad. Sci. USA 84:4767–4771 (1987); Wang, et al., Gene 100: 195–199 (1991). Complete citations of other publications refer to in table are set forth elsewhere in specification.

E. coli strains were grown in LB (10 g of tryptone, 10 g of NaCl, and 5 g of yeast extract per liter). LB broth and LB agar were supplemented with ampicillin (Ap; 100 μg/ml), kanamycin (Kn; 25 μg/ml), Cm (12.5 μg/ml), and 5-bromo-4-chloro-3-indolyl β-D-galactopyranoside (40 μg/ml) as indicated. The iron chelator DP was added to a final concentration of 200 μM to LB agar and as indicated to LB broth.

Nucleic Acids. DNA cloning, plasmid preparation, and DNA sequence analysis were performed according to standard methods (Ausubel, F. M., Brent, R., Kingston, R. E., Moore, D. D., Seidman, J. G., Smith, J. A. & Struhl, K. (1988) Current Protocols in Molecular Biology (Wiley, New York)., Sanger, F., Nicklen, S. & Coulsen, A. R. (1977) Proc. Natl. Acad. Sci. USA 74, 5463–5467). Restriction endonucleases, T4 polynucleotide kinase, and Klenow fragment of DNA polymerase (New England Biolabs) were used according to the manufacturer's specifications. PCR mutagenesis of DtxR was based on the method of Vartanian et al. (Vartanian, J.-P., Henry, S. & Wain-Hobson, S. (1996) Nucleic Acids Res. 24, 2627–2631). In brief, BglII-tagged primers 1515 (5'-ACCAGATCTGCCGAAAAACTTCGA-3' (SEQ ID NO:9)) and 1516 (5'-ACCAGATCTCCGCCTT-TAGTATTTA-3' (SEQ ID NO:10)) were used to PCR amplify dtxR from plasmid pRDA, which carries the wild-type dtxR operon. The products of the amplification then were digested with BglII and either were ligated into BglII-linearized pSC6M1 and were transformed into E. coli TOP10/λRS65T or were ligated into BamHl digested pBR322 and were transformed into E. coli TOP10/λRS65T/pSC6. Iron-independent mutants of DtxR then were selected on LB agar plates supplemented with chloramphenicol and 2,2'-dipyridyl.

β-Galactosidase Assay.

β-galactosidase activity was measured essentially as described by Miller (Miller, J. H. (1972) Experiments in Molecular Genetics (Cold Spring Harbor Lab. Press, Plainview, N-Y)). In brief, 0.5 ml of an overnight culture at $A600$ of =1.0 were lysed by the addition of lysis mix (chloroform:10% SDS, 2:1), vortexing the mixture for 10 sec and transferring 200 μl to 800 μl lacZ buffer (60 mM $Na_2HPO_4$/40 mM $NaH_2PO_4$/10 mM KCl/1 mM $MgSO_4$/50 mM β-mercaptoethanol). The reaction was initiated by adding 200 μl of o-nitrophenyl β-D-galactopyranoside (Sigma) (4 mg/ml). After incubation at room temperature (5 min-1hr), the reaction was stopped by the addition of 0.5 ml of 1M sodium carbonate. Absorbance was measured at 420 and 550 nm, and β-galactosidase units were calculated according to Miller, supra.

Results

Development of the PSDT System.

The PSDT system, which consists of a lysogenic E. coli TOP10 host strain carrying the reporter gene cat on an integrated λ phage, λRS65T, and a set of detector plasmids, is illustrated in FIG. 1. Expression of cat on λRS65T is controlled by the tetA promoter/operator (tetAPO), and, in the absence of the tetracycline repressor (TetR), E. coli TOP10/λRS65T is resistant to chloramphenicol ($Cm^R$).

We next constructed the detector plasmid pSC6, which carries the tetR gene under the control of the diphtheria toxPO. When pSC6 is transformed into E. coli TOP10/

λRS65T, the bacterial host strain becomes Cm-sensitive (Cm$^s$) by virtue of the constitutive expression of tetR, which recognizes and binds to the tetAO and represses cat gene expression. However, if a functional dtxR allele is introduced into the bacterial host on a second compatible plasmid, pRDA, the interaction between DtxR and the toxO will repress the expression of tetR, and the bacterial host, *E. coli* TOP10/λRS65T/pSC6/pRDA, then will regain its CMP phenotype. Furthermore, because the iron chelator 2,2'-dipyridyl (DP) is known to inactivate DtxR, the addition of DP to the growth medium results in a phenotypic conversion from Cm$^R$ to Cm$^S$. As shown in Table 3, the addition of DP to the growth medium did result in the conversion to a 2,2'-dipyridyl Cm$^s$ phenotype.

Finally, to demonstrate the requirement for a functional dtxR in the PSDT system, pRDA was digested with EcoRV to delete a 713-bp fragment and thereby knock out the dtxR gene. The resulting plasmid, pLS-2, then was transformed into *E. coli* TOP10/λRS65T/pSC6. As anticipated, in the absence of a functional DtxR, the indicator strain becomes Cm$^s$. Table 3 summarizes the antibiotic resistance phenotypes of derivatives of *E. coli* TOP10/λRS65T that carry one or more of the PSDT detector plasmids.

In each instance, restriction endonuclease digestion analysis demonstrated that the plasmids had an insertion of the size anticipated for DtxR. Of the nine colonies that were isolated using the PSDT system, four clones subsequently were characterized fully. The plasmids named pSDM2, pSDM3, pSDMl1 and pSDM5 are derivatives of the detector plasmid pSCM61, and pSDM5 was derived from pBR322. The mutant DtxRs encoded by these plasmids were designated SAD2, SAD3, SADl1, and SAD5, respectively.

Figure 2:
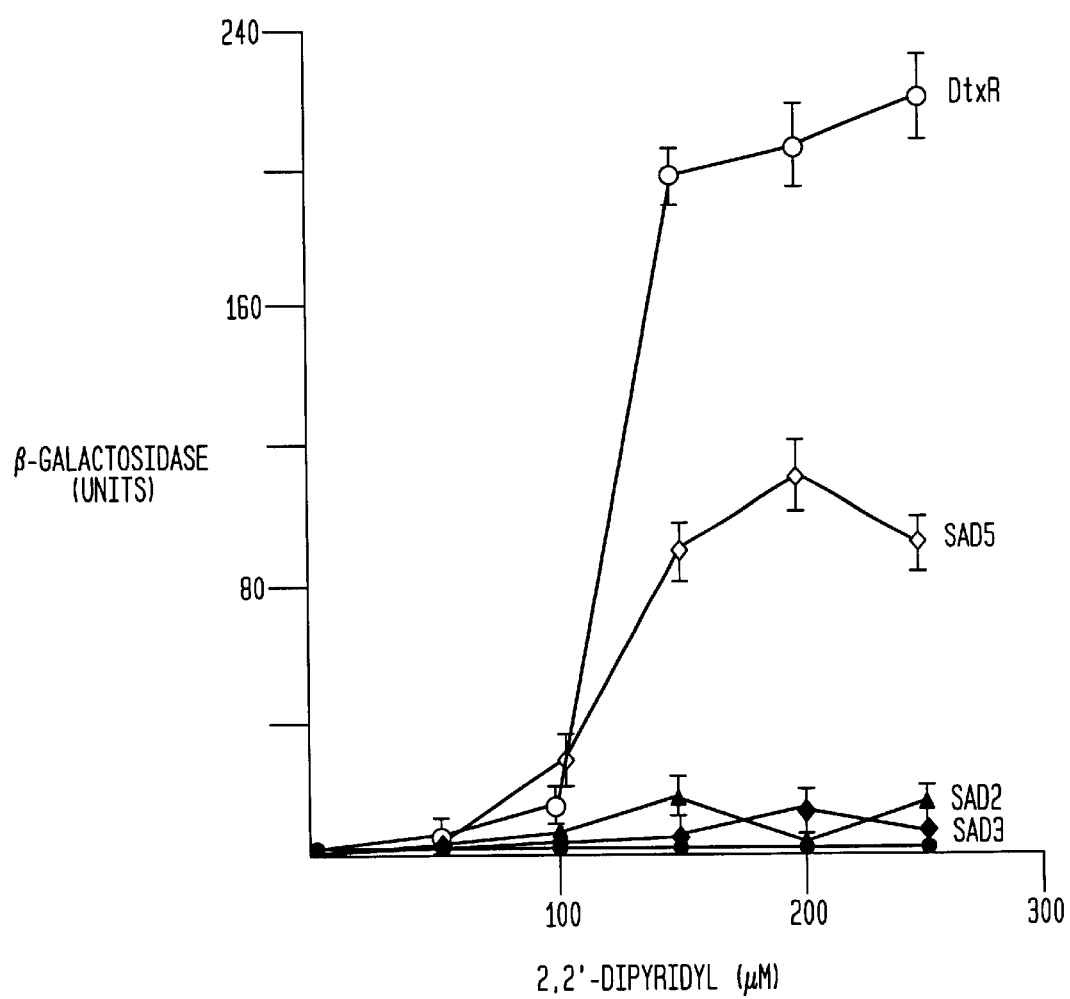
FIG. 2 is a graph of the β-galactosidase activity of E. coli DH5/αRS45T toxPO lacZ that carry plasmid pDRA expressing a wt dtxR gene[open circles], pDM2 [filled diamond], pDM3 [filled triangle], pDM11 [filled circle] or pDM5 [open diamond]. Plasmids pDM2, pDM3, pDM11 and pDM5. The β-galactosidase gene was placed under the control of the toxPO in place of the cat gene. The data show that as iron becomes limiting with the addition of increasing amounts of 2,2'-dipyridyl (DP) to the growth medium β-galactosidase activity increases in cells expressing the wild-type DtxR protein. In contrast, cells expressing mutant iron-independent repressors fail to de-repress the β-galactosidase gene and no β-galactosidase activity is detectable.

To demonstrate that each isolate carried an active iron-independent mutant of dtxR, their respective dtxR alleles were recloned into the NcolBamHl sites of pRDA to replace the wild-type DtxR. The resulting plasmids were designated pDM2, pDM3, pDMl1, and pDM5, respectively. The pDM series of plasmids then were transformed individually into *E. coli* DH5α/RS45toxPO. This reporter strain carries a transcriptional fusion in which the lacZ gene is under the control of the diphtheria toxPO, toxPO-lacZ, and, as a result, the synthesis of β-galactosidase is regulated by their respective dtxR gene products. Individual strains were grown in LB broth supplemented with appropriate antibiotics in either the absence or presence of increasing concentrations of DP. As shown in FIG. 2, β-galactosidase assays indicated that, in

TABLE 3

Antibiotic Resistance Phenotype of Selected Strains and Plasmids Central to Examples 1 and 2

|  | Ap | Kn | Cm | Ap/Kn | Ap/Kn/Cm | Ap/Kn/DP | Ap/Kn/Cm/DP |
|---|---|---|---|---|---|---|---|
| TOP10/λRS65T | − | − | +++ | − | − | − | − |
| pSC6 | − | +++ | − | − | − | − | − |
| pRDA | +++ | − | +++ | − | − | − | − |
| pSC6/pRDA | +++ | +++ | +++ | +++ | +++ | − | − |
| pSC6/pLS-2 | +++ | +++ | +++ | +++ | − | − | − |
| pLS-1/pSA18M1 | +++ | +++ | − | +++ | − | +++ | − |
| pLS-1/pSA20 | +++ | +++ | +++ | +++ | +++ | +++ | − |
| pLS-2/psA20 | +++ | +++ | − | +++ | − | +++ | − |

Isolation of Iron-Independent Self-Activating DtxR (SAD) Mutants.

The PSDT system initially was developed for the positive selection of dtxR alleles, homologues, and DtxR DNA target sites from genomic libraries. We have also used the PSDT system to isolate a unique class of iron-independent, constitutively active mutants of DtxR. For this purpose, we constructed the detector plasmid pSC6M1, in which the introduction of a unique BglII restriction endonuclease site allows the cloning of DtxR alleles in the same vector that carries the toxPO-tetR transcriptional fusion.

The overall scheme for the selection of SAD mutants is shown in FIG. 1. The wild-type DtxR allele carried by pRDA was mutagenized by PCR amplification according to the method of Vartanian et al. (Vartanian, J.-P., Henry, S. & Wain-Hobson, S. (1996) Nucleic Acids Res. 24, 2627–2631) using BglII tagged primers 1515 and 1516. After PCR mutagenesis, the amplified DNA was digested with BglII and either was ligated into the BglII site of pSC6M1 and was transformed into TOP10/λRS65T or was ligated into the BamHl site of pBR322 and was transformed into TOP10/λRS65T/pSC6. Because wild-type DtxR is inactivated in the presence of the iron chelator DP, potential SAD mutants were selected on LB agar supplemented with both Cm and 200 μM DP. In a typical experiment, 10$^5$ colony forming units were plated on LB/Cm/DP agar plates, and after 24-hr incubation at 37° C., the colonies that developed were picked and colony purified, and their respective plasmids were analyzed.

marked contrast to transformants that expressed wild-type DtxR, those strains that expressed either SAD2, SAD11, or SAD3 maintained complete repression of lacZ, even in the presence of 250 μM DP. In contrast, the transformant that expressed SAD5 displayed an intermediate iron-independent phenotype. These results are consistent with the observation that the growth of *E. coli* TOP10/λRS65T /pSC6/pSDM5 is inhibited partially by Cm in the presence of 200 μM DP. In comparison, *E. coli* TOP10/λRS65T strains that carry either pSDM2, pSDM3, or pDMl1 are completely Cm$^R$.

To further demonstrate that SAD2 and SAD3 were iron-independent mutants of dtxR, each allele was knocked out by the deletion of a 713-bp EcoRV restriction endonuclease fragment that encompasses the promoter and N-terminal encoding portion of their structural genes. As anticipated, transformation of *E. coli* DH5α/λRS45toxPO with plasmids encoding defective SAD2 and SAD3 genes failed to confer detectable repression of lacZ (data not shown).

SUMMARY

The positive selection of iron-independent SAD mutants using the PSDT system is based on two sequential levels of gene regulation that lead to cat gene expression and the emergence of a Cm$^R$ phenotype in the *E. coli* indicator strain. In this system, cat gene expression is controlled by TetR, which in turn is regulated by a functional DtxR:toxO circuit. Wild-type DtxR must be activated by Fe(II), or other transition metal ions in vitro, to bind to the toxO. Therefore, the addition of the iron chelator DP to the growth medium results in the inactivation of the repressor. In the PSDT system, addition of DP to the growth medium results in the derepression of tetR and leads to a $Cm^s$ phenotype in the indicator strain. The power of the PSDT selection system is on the order of $10^{-8}$ (data not shown). This system has been used to isolate a class of iron-independent mutants of DtxR that remain constitutively active even in the absence of iron.

The dtxR gene was randomly mutagenized by PCR amplification. After digestion of the amplified DNA with BglII and ligation into the BglII site of pSC6MI, E. coli TOP10/λRS65T was transformed and plated on LB agar supplemented with Cm and 200 μM DP. Alternatively, BglII digested amplified DNA was ligated into the BamHl site of pBR322, E. coli TOP10/λRS65T/pSC6 was transformed, and transformants were selected on LB agar supplemented with Cm and 200 μM DP. By using this system, a total of nine iron-independent SAD mutants were isolated, of which four were characterized extensively.

The independently isolated SAD2, SAD3, and SAD11 mutants were isolated from derivatives of pSC6M1 in the TOP10/λRS65T strain of E. coli. In each instance, the recombinant E. coli expressed one of several mutant iron independent DtxR proteins that demonstrate how alterations of DtxR protein structure can lead to a constant state of repression. These proof of concept experiments serve to support the validity of targeting the DtxR protein with small molecules to induce analogous changes in structure and thereby turn off virulence determinant expression.

Example 2

Example 2: Application of the PSDT Screen for rapid identification of functionally equivalent DtxR homologues and their cognate operator sequences in one step.

As discussed above, several repressors that exhibit considerable nucleotide and amino acid homology to DtxR have been identified and characterized in a number of pathogenic and non-pathogenic bacterial species (Doukhan, L. Predich, M., Nair, G., Dussurget, O., Mandic-Mulec, I., Cole. S.T. Smith, D.R., and Smith, I. (1995) Gene 165:67–70; Schmitt, M.P., Predich, M., Doukhan, L., Smith, I., and Holmes, R.K. (1995) Infect. Immun. 63:4284–4289.; Oguiza, I.A., Tao, X., Marcos, A.T., Martin, J.F., and Murphy, J.R. (1995) J. Bacteriol. 177:465–467; Gunter, K. Toupet, C., and Schupp, T. (1993) J Bacteriol. 175:3295–3302). These repressors have been implicated in the iron dependent gene regulation in their respective hosts of origin (Boyd, J., Oza, M., and Murphy, J.R. (1990) Proc. Natl. Acad. Sci. USA, 87:5968–5972; Schmitt, M.P., and Holmes, R.K. (1991) Infect Immun. 59:1899–1904: Schmitt, M.P., and Holmes, R.K. (1994) J. Bacteriol. 176:1141–1149; Schmitt, M.P., and Holmes, R.K. (1994) J. Bacteriol. 176:1141–1149., Schmitt, M.P. (1997) J. Bacteriol. 179:838–845). Furthermore, table 1 above has indicated an additional collection of bacterial species which have one or more identical copies of the toxO, operator sequence suggesting they may employ an analogous metal activated repressor dependent regulatory mechanism for state specific gene expression.

Given the potentially important role played by DtxR and DtxR homologues in pathogenesis, we have developed a positive genetic selection system for the rapid isolation of functionally equivalent dtxr alleles, dtxR homologues and DtxR-target DNA binding or “iron box” sites. The PSDT system as described above, is used in this example to demonstrate the cloning of dtxR alleles from chromosomal libraries of *C. diphtheriae* and *Brevibacterium ammoniagenes* in a single step using positive selection. We have recently isolated DtxR homologues from *M. tuberculosis* and *M. avium*. The use of the PSDT system in the cloning of DtxR binding sites from oligonucleotide libraries is also demonstrated. In each instance, only, those clones which carry a functional dtxR/DtxR target DNA binding site grow on medium supplemented with chloramphenicol. The utility of the PSDT system for these types of selection is not merely the rapid one step isolation of genes and operator sequences without the complication of PCR induced mutations but in the subsequent ability to modify the PSDT system such that it becomes more finely adjusted to characteristics of a given species specific repressor:operator circuits. This fine tuning can potentially augment the ability to identify compounds capable of activating a repressor in a given species of interest rather than rely upon activators of DtxR or a readily available homologue to serve as activators in the species of interest.

RESULTS AND DISCUSSION

Genetic Construction of the PSDT system

The PSDT system consists of a lysogenic *E. coli* host strain which carries the reporter gene cat on a derivative of coliphage X, *E. coli* TOP10/λRS65T, and a set of detector plasmids. The bacterial strains, plasmids. and coliphage X strains used in this work are listed in Table 2 above. The oligonucleotides encoding the tetracycline resistant determinant gene (tetA) promoter and operator sequence (tetAPO) with EcoRl and BamHl sticky ends.

5'-AATTCGTTGACACTCTATCATTGATAGAGTTATTTAGGATCCA-3' (SEQ ID NO:11);

5'-GATCTGGATCCTAAAATAACTCTATCAATGATAGAGTGTCAACG-3' (SEQ ID NO:12) were synthesized in vitro, purified, annealed, and ligated into the EcoRl and BamHl sites of pRS551 to form pRS61. A promoterless cat gene derived from pCM4 was inserted into the BamHl site of pRS61 to construct pRS64. Plasmid pRS65T was made by eliminating the Kn gene of pRS64 by introducing a HpaI/FspI fragment from plasmid pGPl-2 into the SmaI site, and replacing the 624 bp HpaI fragment in the lacZ gene with a trpA transcription terminator (TC) (Simons, R.W., Houman, F., and Kleckner, N. (1987) Gene 53:85–96.). Plasmid p65T was then crossed with λRS45 in *E. coli* NK7049, and lysogens carrying the desired recombinant prophage. λRS65T, which formed a double crossover between the bla gene and lacZYA, were initially selected as $Cm^R$ colonies on LB/Cm agar, and further verified by their ampicillin sensitive phenotype.

Plasmid pLS-1 was constructed by inserting the entire dtxR operon from pXT102C into the EcoRl and NarI sites of pBR322. Plasmid pLS-2 was isogenic with pLS-1 except that the dtxR gene was knocked out by the deletion of an intragenic EcoRV fragment.

The promoterless tetracycline resistant determinant repressor (tetR) structural gene was obtained by PCR amplification of DNA from *E. coli* MM108 harboring TN10 using the following primers: HincII tagged forward primer: 5'-CGTGGTCAACAAAAATTAGG-3' (SEQ ID NO:13). SacII-tagged backward primer:

5'-ATTCCGCGGTTATGCTGCTA-3' (SEQ ID NO:14). The PCR product was cloned into the PCRII vector using the TA cloning kit. Several positive recombinants were subjected to DNA sequence analysis and one of the clones containing the correct tetR gene was named pCR/tetR. A derivative of pCR/tetR, pCR/tetRT, was constructed by insertion of a universal translation terminator (TL) was formed by annealing oligonucleotides (5'-GTTAACGCTTAATTAATTAAGC-3' (SEQ ID NO:15);

5'-GCTTAATTAATTAAGCGTTAAC-3' (SEQ ID NO:16)) and ligating them into the HincII site.

The construction of plasmid pSA18M1 is as follows: the parental plasmid, pRS551toxPO/dtxR was constructed by inserting the dtxR structural gene on a PvuII fragment of pHH2500 into the SmaI site of pRS551toxPO. The diphtheria tox minor (Boyd, J., Oza, M., and Murphy, J.R. (1990) Proc. Natl. Acad. Sci. USA, 87:5968–5972) promoter (mtP) plus a multiple cloning site (MCS) (5'-AATTCTGCAGGGCATTGATTCAGAGCACCCTTATA ATAGATCTGAGCTCGGTACCCGGG-3' (SEQ ID NO:17)) and its complementary strand (5'-GATCCCCGGGTACCGAGCTCAGATCTATTATAAGG GTGCTCTGAATCAATGCCCTGCAG-3' (SEQ ID NO: 18)) were synthesized as two oligonucleotides with sticky EcoRI and BamHl ends. After annealing and phosphorylation, the double stranded oligonucleotides were ligated into the EcoRI and BamHl sites of pRS551toxPOIdtxR. The resulting plasmid was named pLS500. The tetR gene plus its upstream TL, carried on a HincII/SacII fragment, was excised from pCP/tetRT and ligated into the SmaI/SacII sites of pLS500 to construct pLS501. A transcription terminator (TC) (5'-GGCAGATAACCAACGCAACGACCCAGCTTCGGCT GGGTTTATCAG-3' (SEQ ID NO: 19)) derived from the ant gene of the Salmonella phage P22 was inserted between the SacI and PvuII sites of pLS501, resulting in plasmid pLS502. Plasmid pLS502 was digested with HindIII and PvuII and the 2.2 kb tetR-bearing fragment was ligated with the 3.1 kb colE1 ori-bearing Hindll/Pvull fragment derived from pRS551, generating pLS503. Plasmid pLS503 was then digested with ScaI and PvuII and the 3.7 kb fragment containing the Kn gene, mtP, and tetR was purified and ligated with the 3.6 kb PvuII fragment from plasmid pWSK129 carrying the replication origin of pSC101 to construct plasmid pSA18. Plasmid pSA18M was created by inserting an EcoRl site at the MCS of pSA18.

Plasmid pSA20 is isogenic with pSA18M1, except that pSA20 has two copies of the dtxR operator sequence inserted upstream of the tetR gene. Plasmid pSC6M1 was constructed by replacing mtP in pSA18M1 with the wild type diphtheria tox promoter/operator sequence (toxPO) from pRS551toxPO and then inserting a 220 bp DNA fragment containing BamHI SmaI, and BqiII sites into the HincII site.

Development and Rationale of the PSDT system

Figure 3:
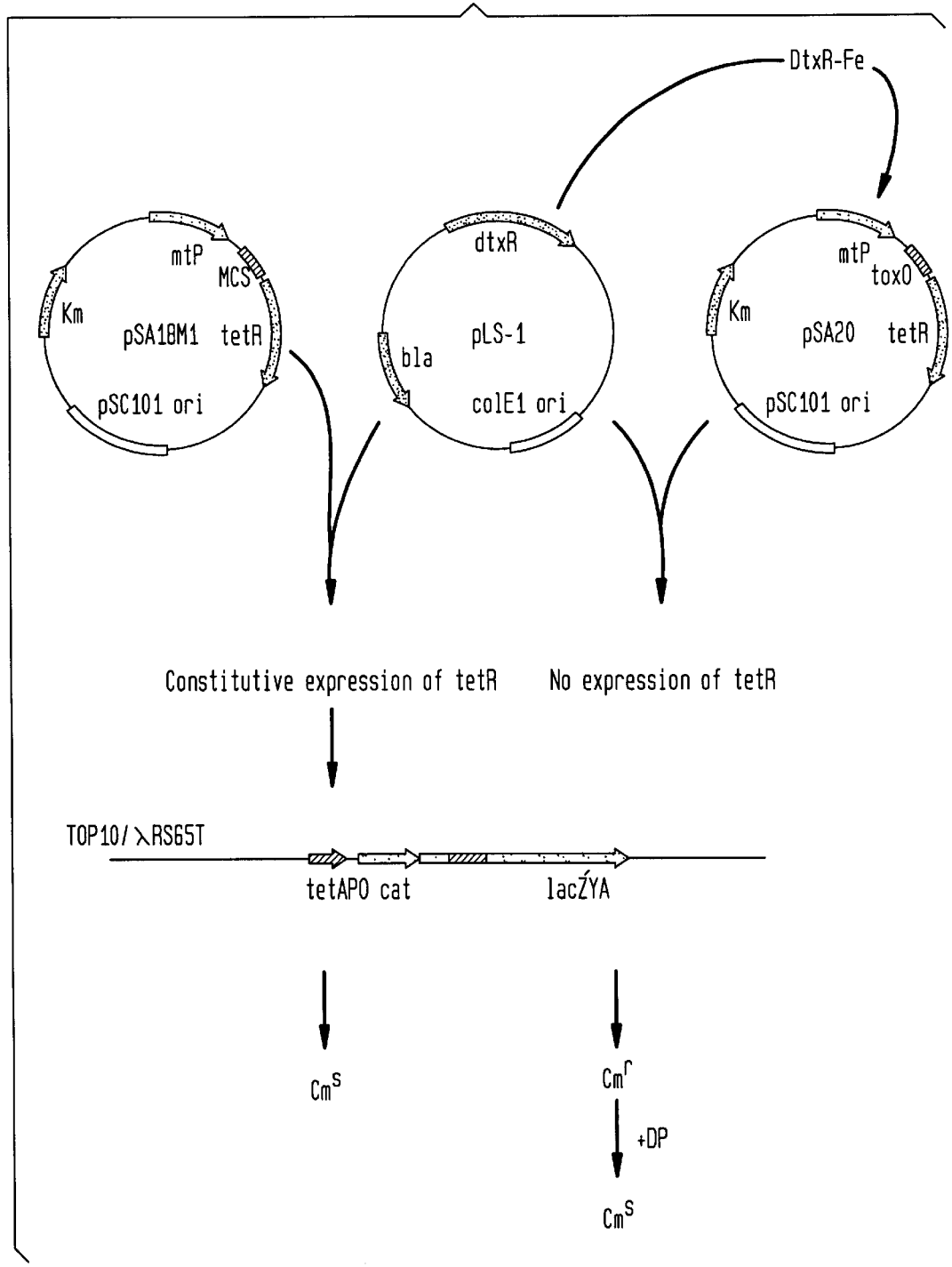
FIG. 3 is a schematic diagram of the PSDT system for the positive selection of DtxR binding sites or DtxR homologues. In the Presence of a functional DtxR-toxO circuit (pLS-1/pSA20) the tetR gene, carried by coliphage λRS65T, is repressed. Repression of TetR synthesis allows the de-repression of the cat gene which confers chloramphenicol resistance to the bacterial host, E. coli TOP1O. In the absence of either a dtxR target operator sequence (pLS-1/pSA18M 1) or DtxR, the constitutive expression of TetR represses the cat gene thereby rendering the bacterial host chloramphenicol sensitive even in the presence of 200 μM 2,2'-dipyridyl.

The detector plasmids in the PSDT system that are used for the selection of DtxR binding sites are pSA18M1 and pLS-1 similar to pSC6M1. The overall principle underlying the PSDT system is shown in FIG. 3. In order to determine whether the PSDT system would operate as designed, we synthesized a linker that encoded the wild type toxO and ligated it into the MCS of pSA18M1. The resultant plasmid. pSA20. when transformed into E. coli TOP10/ λRS65T/pLS-1, conferred a $Cm^R$ phenotype to the host. To examine whether Cm resistance was mediated by DtxR, the transformants were plated on LB agar supplemented with Ap/Kn, Ap/Kn/DP, Ap/Kn/Cm and Ap/Kn/Cm/DP. As shown in Table 3, in marked contrast to the growth observed on Ap/Kn, Ap/Kn/DP and Ap/Kn/Cm plates, E. coli TOP10/λRS65T/pLS-1/pSA20 failed to grow on Ap/Kn/Cm/DP. These results strongly suggested that a functional DtxR: toxO genetic switch was required to establish a $Cm^R$ phenotype. To further demonstrate that this was the case, the dtxR gene in pLS-1 was knocked out by an internal deletion of an EcoRV fragment to form pLS-2. As anticipated, in the absence of DtxR, E. coli TOP10/λRS65T/pLS-2/pSA20 is $Cm^S$. Thus the PSDT system can be utilized to clone unique DtxR homologues or metal dependent regulatory proteins which recognize toxO, or employed to identify novel operator sequences that are functionally recognized by DtxR or DtxR homologues in vivo.

Screening random oligonucleotide libraries for DtxR target sites.

Having demonstrated the feasibility of the PSDT in a model system, we tested its general utility by applying it to the task of selecting DtxR targets from pools of random oligonucleotides generated by PCR. Tao and Murphy (Tao, X., and Murphy, J.R. (1994) Proc. Natl. Acad. Sci., USA. 91:9646–9650) have previously shown that DtxR-mediated affinity selection could be used in vitro to enrich families of oligonucleotides which contain the minimal essential sequence for DtxR recognition. Each of these libraries contains relatively low numbers of high affinity DtxR binding sites in a universe of greater than $10^{10}$ sequences. Oligonucleotide families from round 8, 9 and 11 of in vitro selection were each re-amplified by PCR for an additional 30 cycles. These libraries are related to each other in a hierarchical way in both the abundance of potential DtxR binding sites and their relative affinity to bind DtxR. After purification and digestion with EcoRI and BamHI, the PCR products were then ligated into the MCS of pSA18M1. Ligation mixtures were then transformed into E. coli TOP10/λRS65T/pLS-1 and selected on Ap/Kn/Cm medium. Representative colonies that grew were then subjected to further analysis.

In order to determine whether the $Cm^R$ clones contained authentic DtxR binding sites, individual transformants were first examined for their sensitivity to 2,2'-dipyridyl. Representative colonies were replicate plated on LB agar supplemented with either Ap/Kn, Ap/Kn/DP, Ap/Kn/Cm, or Ap/Kn/Cm/DP, and their growth was carefully monitored. As anticipated, all colonies exhibited robust growth on AP/Kn, Ap/Kn/DP, and Ap/Kn/Cm plates. In contrast, the growth of all colonies was either severely retarded or completely inhibited on LB agar plates supplemented with Ap/Kn/Cm/DP. Subsequent DNA sequence analysis indicated that in general, the DtxR target sites selected from PCR rounds 8, 9 and 11, shared 67–77% (data not shown), 70–80% (data not shown ) and 85% (data not shown) identity with toxO respectively. Moreover, DNA sequence analysis demonstrated that all selected clones carried DtxR binding sites that possessed the minimal essential nucleotides required for DtxR binding. Most importantly, the PSDT system allowed for the direct selection of clones which carried functional DtxR sensitive operators from complex oligonucleotide libraries.

Positive selection of dtxR alleles and homologues from Corynebacterium diphtheriae and Brevibacterium amuioniagenes genomic libraries.

The PSDT system was then employed for the positive selection of dtxR alleles and homologues from genomic libraries. The detector plasmid used in this system is pSC6M1, a derivative of pSA18M1 that carries a single copy of toxPO which directs the expression of tetR. We first attempted to clone dtxR alleles from two different epidemic strains of C. diphtheriae recently isolated from Russia and Ukraine (Nakao, H., Pruckler, J.M., Mazurova, I.K., Narvskaia, O.V., Glushkevich, T., Marijevski, V.F., Kravetz, A.N., Fields, B.S., Wachsmuth, I.K., and Popovic, T. (1996) J. Clin. Microbiol. 34:1711–1716.,Nakao, H., Mazurova, I.K, Glushkevich, T., and Popovic, T. (1997) Res. Microbiol. 148:5–54.). Chromosomal DNA from each strain was isolated, digested partially with Sau3Al, and then ligated into the BglII site of pSC6M1 E. coli TOP10/λRS65T was transformed, and the transformants were selected on LB agar supplemented with Kn/Cm. Four to five colonies were readily obtained from each selection, and, as anticipated all were dtxR positive by both PCR analysis using dtxR specific primers and by DNA sequence analysis.

We then tested the cross-genus applicability of the PSDT system by attempting to clone the dtxR homologue from a genomic library of *B. ammoniagenes*. The molecular cloning and selection were conducted as described above. Each of the four $Cm^R$ colonies that grew on Cm supplemented medium carried a complete dtxR operon as demonstrated by DNA sequence analysis. The analysis showed that with the exception of a T to G transversion at 372, the structural gene of the DtxR homologue of *B. ammoniogenes* is identical to that of *B. lactofermentum* (Oguiza, I.A., Tao, X., Marcos, A.T., Martin, J.F., and Murphy, J.R. (1995) J. Bacteriol. 177:465–467).

Several techniques have been described previously which meet similar objectives as the PSDT system. For example, SELEX (systematic evolution of ligands by exponential enrichment) (Ochsner, U.A., and Vasil, M.L. (1996) Proc. Natl. Acad. Sci., USA. 93:4409–4414) and MuST (multiplex selection technique) (Nallur, G.N., Prakash, K., & Weissman, S.M. (1996) Proc. Natl. Acad. Sci., USA. 93:1184–1189.) are in vitro selection, procedures devised for the identification of regulatory protein target sites based on DNA-protein interaction. FURTA (Fur titration assay) (Stojiljkovic, L. Baumler, A.J., and Hantke, K. (1994) J. Mol. Biol. 236:531–545) is a genetic screen for the detection of Fur-binding activities based on the competition of a fur-box carried on a high-copy plasmid with the single-copy chromosomal Fur-box for Fur. Other methods relying on the activation of a promoterless lacZ gene and subsequent selection of the desired genes based on β-galactosidase/X-gal color reaction have also been developed (Schmitt, M.P., Predich, M., Doukhan, L., Smith, I., and Holmes, R.K. (1995) Infect. Immun. 63:4284–4289.). Although all of these systems have successfully identified numerous genes from both Gram positive and Gram negative organisms, their execution requires multiple selection steps, and, in some cases, the use of non-neutralizing monoclonal antibodies.

An ingenious strategy to select DNA-binding proteins involves the use of a challenge phage vector, P22 Kn9 arc-amHI605 which carries a substitution of a synthetic DNA-binding site for the Mnt operator (Benson, N., Sugiono, P., Bass, S., Mendelman, L.V.. and Youderian, P. (1986) Genetics 114:1–14). Occupancy of the DNA-binding site by the cognate protein will rescue the host from P22 phage lysis. This system relies upon sensitive strains of Salmonella as the host. The current state of the art in this technique involves the use of PCR to amplify a target gene using primers designed from conserved nucleotide sequences of the cloned members of the gene family.

In order to facilitate the cloning of both functional dtxR alleles/homologues and DtxR target sites, we developed the PSDT system. As described, we were readily able to select DtxR binding sites from three oligonucleotide libraries each representing a universe of greater than $10^{10}$ sequences, and to clone and directly select dtxR alleles from genomic digests of *C. diphtheriae* and *B. ammoniagenes* in a single step. We expect, with little modification, the PSDT system can be used in the study of a variety of repressor/operator interactions.

While not intending to be bound by any particular theory of operation, Applicant believes that the self-activating properties exhibited by the DtxR mutants, e.g., SAD2, suggest an intramolecular process involving interaction between or among different domains of DtxR, and that peptides or other substances that mimic such activating effects will be candidates for new classes of antibiotics which phenotypically convert prokaryotic pathogens such as bacteria into non-pathogens. These antibiotics are expected to have medicinal value to both humans and animals.

All publications cited in the specification are indicative of the level of skill of those skilled in the art to which this invention pertains. All these publications are herein incorporated by reference to the same extent as if each individual publication were specifically and individually indicated to be incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A method for identifying a non-metal ion activator of a transition metal-dependent repressor of gene expression in a prokaryote, comprising:

(a) providing recombinant cells comprising a first recombinant DNA segment containing a first promoter operably linked to a first regulatory gene encoding a first repressor native to or functional in a given prokaryote, a second DNA segment containing a second promoter operably linked to a first operator that binds said first repressor and a second regulatory gene encoding a second repressor, and a third recombinant DNA segment comprising a third promoter operably linked to a second operator that binds the second repressor, and a reporter gene;

(b) culturing said recombinant cells in medium substantially free of metal ion activators of said first repressor and which contains a selection agent that directly or indirectly causes a detectable response upon expression or lack of expression of the reporter gene;

(c) adding a non-metal ion test substance to said medium; and (d) determining whether the response occurs as an indication of whether said test substance activates said first repressor.

2. The method of claim 1 wherein said first regulatory gene encodes a diphtheria tox repressor (DtxR) protein and said first operator binds said DtxR protein.

3. The method of claim 2 wherein said first regulatory gene encodes DtxR and said first operator comprises native tox operator, a functional fragment of said operator or a variant of a DtxR consensus binding sequence.

4. The method of claim 1 wherein said first regulatory gene encodes a diphtheria tox repressor (DtxR) homologue and said first operator binds said DtxR homologue.

5. The method of claim 4, wherein said DtXR homologue is an iron dependent regulator (IdeR) and said first operator binds said IdeR.

6. The method of claim 1, wherein said first repressor encodes ferric uptake regulator (Fur).

7. The method of claim 1 wherein said second regulatory gene encodes TetR and said second operator comprises teto.

8. The method of claim 1 wherein said reporter gene encodes chloramphenicol acetyltransferase and said selection agent is chloramphenicol.

9. The method of claim 1 wherein said medium comprises a chelating agent that binds metal ion activators of said first repressor.

10. The method of claim 9 wherein said chelating agent is 2,2'-dipyridyl.

11. The method of claim 1 wherein said first and second recombinant DNA segments are contained in a first vector and said third recombinant DNA segment is contained in a second vector.

12. The method of claim 11 wherein said second vector is a lambda phage.

13. The method of claim 1 wherein said cells are *E. coli* cells.

14. A method for identifying a non-metal ion activator of a diphtheria tox repressor (DtxR) protein in a prokaryote, comprising:

(a) providing recombinant cells comprising a recombinant vector, wherein said vector comprises a first DNA segment containing a first promoter operably linked to a first regulatory gene encoding a DtxR protein, a second DNA segment comprising a second promoter operably linked to an operator that binds said DtxR protein and a second regulatory gene encoding a tetracycline repressor (TetR), and a third DNA segment comprising a third promoter operably linked to a tetracycline operator (tetO) and a reporter gene encoding chloramphenicol acetyltransferase;

(b) culturing said recombinant cells in medium substantially free of metal ion activators of said DtxR protein and which comprises chloramphenicol;

(c) adding a test substance to said medium; and (d) determining the extent of growth of said cells as an indication of whether said test substance activates said DtxR protein.

15. A method for identifying a non-metal ion activator of a metal-dependent repressor of gene expression in a prokaryote, comprising: providing a solution containing (a) purified repressor native to or functional in a given prokaryote; (b) a DNA construct comprising in operable association, a promoter, an operator and a reporter gene; (c) a coupled transcriptional and translational system that allows expression of said reporter gene; (d) a chelating agent that binds metal activators of said repressor; and (e) a non-metal test substance to allow a reaction to occur; and detecting expression or lack of expression of said reporter gene as an indication of whether the test substance activates said repressor.

16. The method of claim 15 wherein the coupled transcriptional and translational system comprises bacterial extract.

17. The method of claim 15 wherein said reporter gene encodes P-galactosidase or luciferase.

* * * * *

UNITED STATES PATENT AND TRADEMARK OFFICE
CERTIFICATE OF CORRECTION

PATENT NO. : 6,309,817 B1
DATED : October 30, 2001
INVENTOR(S) : John Murphy and Li Sun It is certified that error appears in the above-identified patent and that said Letters Patent is hereby corrected as shown below:

Column 3,
Line 18, "(toxo) or a toxo fragment" should read -- (toxO) or a toxO fragment --

Column 4,
Line 26, "DH5/αRS45T" should read -- DH5αC/λRS45T --.

Column 7,
Line 8, "toxO sequences" should read -- toxO like sequences --.
Line 32, "$P_{tox}$" should read -- $P_{TOX}$ --.

Column 8,
Line 24, "toxo" should read -- toxO --.

Column 10,
Line 36, "$10^5$" should read -- $10^{-5}$ --.

Column 16,
Line 16, "DH5α/RS45toxPO" should read -- DH5α/λRS45toxPO --.

Column 17,
Line 63, "dtxr" should read -- dtxR --.

Column 18,
Line 24, "coliphage X" should read -- coliphage λ --.
Line 25, "coliphage X" should read -- coliphage λ --.
Line 61, "PCRII" should read -- pCRII --.

Column 29,
Line 21, "DtXR" should read -- DtxR --.
Line 27, "teto" should read -- tetO --.

UNITED STATES PATENT AND TRADEMARK OFFICE
CERTIFICATE OF CORRECTION

PATENT NO. : 6,309,817 B1
DATED : October 30, 2001
INVENTOR(S) : John Murphy and Li Sun It is certified that error appears in the above-identified patent and that said Letters Patent is hereby corrected as shown below:

<u>Column 30,</u>
Line 39, "P-galactosidase" should read -- β-galactosidase --.

Signed and Sealed this

Twenty-eighth Day of May, 2002

Attest:

JAMES E. ROGAN
*Attesting Officer*    *Director of the United States Patent and Trademark Office*

SEQUENCE LISTING

<160> NUMBER OF SEQ ID NOS: 19

<210> SEQ ID NO 1
<211> LENGTH: 27
<212> TYPE: DNA
<213> ORGANISM: Corynebacterium diphtheriae

<400> SEQUENCE: 1
ataattagga tagctttacc taattat                27

<210> SEQ ID NO 2
<211> LENGTH: 19
<212> TYPE: DNA
<213> ORGANISM: Unknown
<220> FEATURE:
<223> OTHER INFORMATION: Description of Unknown Organism:
      Oligonucleotide

```
<400> SEQUENCE: 2
gtaggttagg ctaacctat                                              19

<210> SEQ ID NO 3
<211> LENGTH: 25
<212> TYPE: DNA
<213> ORGANISM: Unknown
<220> FEATURE:
<223> OTHER INFORMATION: Description of Unknown Organism:
      Oligonucleotide
<223> OTHER INFORMATION: "n" bases represent a, t, c, g, other or
      unknown

<400> SEQUENCE: 3
ananttaggn tagnctannc tnnnn                                       25

<210> SEQ ID NO 4
<211> LENGTH: 19
<212> TYPE: DNA
<213> ORGANISM: Unknown
<220> FEATURE:
<223> OTHER INFORMATION: Description of Unknown Organism:
      Oligonucleotide

<400> SEQUENCE: 4
twaggttags ctaacctwa                                              19

<210> SEQ ID NO 5
<211> LENGTH: 20
<212> TYPE: DNA
<213> ORGANISM: Unknown
<220> FEATURE:
<223> OTHER INFORMATION: Description of Unknown Organism:
      Oligonucleotide

<400> SEQUENCE: 5
gataattgag aatcattttc                                             20

<210> SEQ ID NO 6
<211> LENGTH: 19
<212> TYPE: DNA
<213> ORGANISM: Unknown
<220> FEATURE:
<223> OTHER INFORMATION: Description of Unknown Organism:
      Oligonucleotide

<400> SEQUENCE: 6
gatattgaga atcattttc                                              19

<210> SEQ ID NO 7
<211> LENGTH: 19
<212> TYPE: DNA
<213> ORGANISM: Unknown
<220> FEATURE:
<223> OTHER INFORMATION: Description of Unknown Organism:
      Oligonucleotide

<400> SEQUENCE: 7
gatactgaga atcattttc                                              19

<210> SEQ ID NO 8
<211> LENGTH: 19
<212> TYPE: DNA
<213> ORGANISM: Unknown
<220> FEATURE:
<223> OTHER INFORMATION: Description of Unknown Organism:
      Oligonucleotide
```

```
<400> SEQUENCE: 8
gatactgaga atcatgttc                                                    19

<210> SEQ ID NO 9
<211> LENGTH: 24
<212> TYPE: DNA
<213> ORGANISM: Unknown
<220> FEATURE:
<223> OTHER INFORMATION: Description of Unknown Organism:
      Oligonucleotide

<400> SEQUENCE: 9
accagatctg ccgaaaaact tcga                                              24

<210> SEQ ID NO 10
<211> LENGTH: 25
<212> TYPE: DNA
<213> ORGANISM: Unknown
<220> FEATURE:
<223> OTHER INFORMATION: Description of Unknown Organism:
      Oligonucleotide

<400> SEQUENCE: 10
accagatctc cgcctttagt attta                                             25

<210> SEQ ID NO 11
<211> LENGTH: 44
<212> TYPE: DNA
<213> ORGANISM: Unknown
<220> FEATURE:
<223> OTHER INFORMATION: Description of Unknown Organism:
      Oligonucleotide

<400> SEQUENCE: 11
aattcgttga cactctatca ttgatagagt tattttagga tcca                        44

<210> SEQ ID NO 12
<211> LENGTH: 44
<212> TYPE: DNA
<213> ORGANISM: Unknown
<220> FEATURE:
<223> OTHER INFORMATION: Description of Unknown Organism:
      Oligonucleotide

<400> SEQUENCE: 12
gatctggatc ctaaaataac tctatcaatg atagagtgtc aacg                        44

<210> SEQ ID NO 13
<211> LENGTH: 20
<212> TYPE: DNA
<213> ORGANISM: Unknown
<220> FEATURE:
<223> OTHER INFORMATION: Description of Unknown Organism:
      Oligonucleotide

<400> SEQUENCE: 13
cgtggtcaac aaaaattagg                                                   20

<210> SEQ ID NO 14
<211> LENGTH: 20
<212> TYPE: DNA
<213> ORGANISM: Unknown
<220> FEATURE:
<223> OTHER INFORMATION: Description of Unknown Organism:
      Oligonucleotide
```

```
<400> SEQUENCE: 14
attccgcggt tatgctgcta                                                      20

<210> SEQ ID NO 15
<211> LENGTH: 22
<212> TYPE: DNA
<213> ORGANISM: Unknown
<220> FEATURE:
<223> OTHER INFORMATION: Description of Unknown Organism:
      Oligonucleotide

<400> SEQUENCE: 15
gttaacgctt aattaattaa gc                                                   22

<210> SEQ ID NO 16
<211> LENGTH: 22
<212> TYPE: DNA
<213> ORGANISM: Unknown
<220> FEATURE:
<223> OTHER INFORMATION: Description of Unknown Organism:
      Oligonucleotide

<400> SEQUENCE: 16
gcttaattaa ttaagcgtta ac                                                   22

<210> SEQ ID NO 17
<211> LENGTH: 59
<212> TYPE: DNA
<213> ORGANISM: Unknown
<220> FEATURE:
<223> OTHER INFORMATION: Description of Unknown Organism:
      Oligonucleotide

<400> SEQUENCE: 17
aattctgcag ggcattgatt cagagcaccc ttataataga tctgagctcg gtacccggg          59

<210> SEQ ID NO 18
<211> LENGTH: 59
<212> TYPE: DNA
<213> ORGANISM: Unknown
<220> FEATURE:
<223> OTHER INFORMATION: Description of Unknown Organism:
      Oligonucleotide

<400> SEQUENCE: 18
gatccccggg taccgagctc agatctatta taagggtgct ctgaatcaat gccctgcag          59

<210> SEQ ID NO 19
<211> LENGTH: 45
<212> TYPE: DNA
<213> ORGANISM: Unknown
<220> FEATURE:
<223> OTHER INFORMATION: Description of Unknown Organism:
      Oligonucleotide

<400> SEQUENCE: 19
ggcagataac caacgcaacg acccagcttc ggctgggttt atcag                         45
```